United States Patent [19]

Papaconstantin et al.

[11] Patent Number: 4,997,649
[45] Date of Patent: Mar. 5, 1991

[54] **COSMETIC AND DERMATOLOGICAL COMPOSITIONS INCLUDING AN EXTRACT OF *SILYBUM MARIANUM* RICH IN SILYMARINE ASSOCIATED WITH ESSENTIAL FATTY ACIDS**

[75] Inventors: Elisabeth Papaconstantin; Philippe Lepage, both of Paris; Pascale Frerejouand, Levallois Perret; Jean-Pierre Marty, Montesson, all of France

[73] Assignee: Parfums Rochas, Paris, France

[21] Appl. No.: 499,552

[22] Filed: Mar. 26, 1990

Related U.S. Application Data

[63] Continuation of Ser. No. 145,146, Jan. 19, 1988, abandoned.

[30] Foreign Application Priority Data

Jan. 19, 1987 [FR] France ................................ 87 00550
Apr. 10, 1987 [FR] France ................................ 87 05089

[51] Int. Cl.$^5$ ........................ A61K 7/02; A61K 35/12
[52] U.S. Cl. ................................ 424/195.1; 514/458; 514/558
[58] Field of Search ............... 424/195.1; 514/458, 514/558

[56] References Cited

U.S. PATENT DOCUMENTS

| | | | |
|---|---|---|---|
| 4,661,343 | 4/1987 | Zabotto et al. | 514/844 X |
| 4,666,701 | 5/1987 | Horrobin et al. | 424/10 |
| 4,702,913 | 10/1987 | Marty | 424/95 |
| 4,749,573 | 6/1988 | Bonne et al. | 424/195.1 |

FOREIGN PATENT DOCUMENTS

| | | |
|---|---|---|
| 0180505 | 5/1986 | European Pat. Off. . |
| 0236218 | 9/1987 | European Pat. Off. . |
| 2334652 | 1/1975 | Fed. Rep. of Germany ... 424/195.1 |

OTHER PUBLICATIONS

Lust, *The Herb Book*, pp. 128, 182–183 (1974).
Williams, *Chem. Abs.*, 83, 15501b (1975).
The Merck Index, Ninth Ed., pp. 8283, 9699 (1976).
Translation of a page from the *Journal of Applied Cosmetology International Journal of Cosmetics Science*, 3, pp. 83–93 (1981).

*Primary Examiner*—Lester L. Lee
*Assistant Examiner*—S. G. Marshall
*Attorney, Agent, or Firm*—Sandler, Greenblum & Bernstein

[57] ABSTRACT

Cosmetological or dermatological compositions for skin care, principally comprising a mixture comprising:
(A) an extract of *Silybum marianum* fruits rich in Silymarine referred to as "Absolute Hawthorn",
(B) one or more essential polyunsaturated fatty acids containing 18–22 atoms of carbon having only:
either in the free form (1),
or in the form of salts of an alkaline metal or ammonium (2),
or in the form of triglycerides (3),
or in the form of a mixture constituted by two of the three forms (1), (2), and (3), or by the three forms (1), (2), and (3).

21 Claims, No Drawings

COSMETIC AND DERMATOLOGICAL COMPOSITIONS INLCUDING AN EXTRACT OF *MARIANUM SILYBUM* RICH IN SILYMARINE ASSOCIATED WITH ESSENTIAL FATTY ACIDS

This application is a continuation of application Ser. No. 07/145,146, filed Jan. 19, 1988, now abandoned.

BACKGROUND OF THE INVENTION

1. Field of the Invention

The invention relates to novel cosmetic or dermatological compositions including an extract of *Silybum Marianum* fruits which are rich in Silymarine associated with essential fatty acids 2. Description of Background and Relevant Information The extract of *Silybum Marianum* called "Absolute Hawthorn" is a substance which blocks the formation of free radicals. A free radical is an atom or molecule which has transitionally acquired an unassociated electron This unpaired electron has a reverse spin, and confers a very high reactivity to the radical, i.e., a great capacity to react with surrounding molecules which will in turn become free radicals.

This mechanism makes it possible to explain the very high toxicity of these "excited molecules". It is thus that the free radicals will attack key elements of the cell such as the nucleus, proteins and more particularly the membrane.

Yet, the essential fatty acids are the components of the phospholipide membranes and are particularly vulnerable to the free radicals, at their double bonds.

It should be remembered that these carbon-carbon double bonds assure the membrane structure and solidity. The intervention of the free radicals will introduce breaks, angulation modifications which render the membrane less solid, less fluid and less capable of assuring the regulation of the ionic movements.

These membrane alterations will disturb the metabolism of the cell. Less well protected, less well oxygenated, and more poorly nourished, the cell will slowly lose its ability to multiply, will sclerose and then die. It is thus that the free radicals and the processes of peroxydation which they cause, play a significant role in the aging of the cells and then the skin.

It is thus particularly desirable to combine in a cosmetic or dermatological composition "the Absolute Hawthorn", a particularly effective trap of free radicals, which acts in a preventive manner, with the essential fatty acids which have a repairing role.

SUMMARY OF THE INVENTION

It is thus an object of the invention to provide cosmetic or dermatological compositions for the care of the skin, characterized in that they include as a principle component a mixture which comprises:
(A) an extract of *Silybum Marianum* fruits which are rich in Silymarine called "Absolute Hawthorn";
(B) one or more polyunsaturated essential fatty acids containing 18-22 carbon atoms which are present only
 either in the free form (1)
 or in the form of alkaline metal or ammonium salts (2);
 or in the form of triglycerides (3) or present in the form of a mixture composed of two of the three forms (1) (2) and (3) or by the three forms (1) (2) and (3).

It is more particularly an object of the invention to provide compositions, characterized in that component B) is composed of polyunsaturated essential fatty acids containing 18-22 carbon atoms present both in the free form (1) and in the form of triglycerides (3) and in the form of alkaline metal or ammonium salts (2) resulting from the saponification of all or a portion of the triglycerides (3).

Furthermore, it is particularly preferable to add to component A) of the compositions of the invention other substances which trap free radicals to reinforce the action of the "Absolute Hawthorn".

These substances are for example essential olefinic, acyclic, or cyclic terpene oils and their alcohol derivatives and flavonoids. The molecular structure of these compositions makes it possible to explain their free radical trapping role.

One can add for example vitamin E or alphatocopherol, vitamin C, and vitamin A and its derivatives, whose anti-oxidizing and anti-radical properties are well known.

The invention relates more particularly to compositions characterized in that component (A) furthermore includes essential terpene oils, flavonoids, alpha-tocopherol.

The invention likewise has as an object to provide compositions characterized in that they include as a principle component about 0.5-10% by weight of the mixture which comprises:
about 10-30% by weight of Silybym Marianum extract;
about 5-15% by weight of essential terpene oils;
about 5-15% by weight of flavonoids;
about 5-20% by weight of alpha-tocopherol;
about 25-40% by weight of triglycerides of essential fatty acids (3);
about 10-25% by weight of essential fatty acids in the free form, preferably gamma linolenic acid (1) and in the form of salts of an alkaline metal or ammonium (2) which can be formed for example entirely or in part by the saponification of the triglycerides (3).

The mixture such as defined above containing about 25-40% of borage oil is registered under the mark SKINAVENGER (Registered Trademark).

In these compositions the gamma linolenic acid (1) in the form of salts of an alkaline metal or ammonium (2) results preferably from the saponification of onagra oil.

The present application also relates to compositions characterized in that they include as a principle component the mixture comprising:
about 1-10% by weight of onagra oil; and
about 1-10% by weight of the mixture which itself comprises about 5% of a dry extract of delipidated fruits of *Silybum Marianum* and about 0.05-2% by weight of alpha-tocopherol, in polyethylene glycol The present application has more particularly as an object compositions characterized in that they include as a principle component the mixture comprising:
about 5% by weight of onagra oil;
about 5% by weight of a mixture which is itself constituted by:
about 5% of a dry extract of delipidated fruits of *Silybum Marianum*; and
about 1% by weight of alpha-tocopherol, in polyethylene glycol;
about 1-10% by weight of UVA-UVB solar filters; and
about 1-10% by weight of spleen extract.

The mixture composed of about 5% by weight of a dry extract of delipidated fruits of Silybum Marianum and of 1% by weight of alpha-tocopherol in polyethylene glycol is registered under the mark FLAVO-PHEROL (Registered Trademark).

The compositions such as defined above have the advantage of including in component A as well as in component B certain soluble substances in an oily phase and other soluble substances in an aqueous phase.

Thus, "Absolute Hawthorn" is water soluble, the essential terpene oils, flavonoids and alphatocopherol are oil soluble. Likewise, triglycerides of essential fatty acids are oil soluble, while free essential fatty acids or fatty acids in the form of salts are water soluble.

In component B, the triglycerides of the essential fatty acids are common synthesized triglycerides. These triglycerides can be obtained by means of one or more sources which include them in a natural state. Such sources are essentially vegetable oils. By way of example, such oils include wheat germ oil, olive oil, corn oil, sunflower oil, sweet almond oil, onagra oil, borage oil, black currant seeds. All of these oils contain very variable proportions of one or more essential fatty acids.

The saponification of the triglycerides occurs by conventional methods, particularly by an alkaline metal hydroxide (sodium or potassium).

This saponification occurs in the presence of an antioxidizer given the great oxidation tendency of polyunsaturated fatty acids.

The polyunsaturated fatty acids which are present in the form of an alkaline metal salt, contained in component B, are preferably salts of sodium or potassium.

There exist two essential polyunsaturated acid families, the gamma-linolenic family and the linoleic family.

The most abundant essential fatty acids at the skin level have as a precursor the metabolized linoleic acid according to the following sequence:

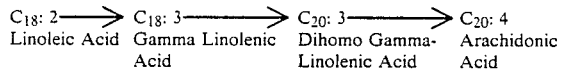

| $C_{18}: 2$ | $\rightarrow$ | $C_{18}: 3$ | $\rightarrow$ | $C_{20}: 3$ | $\rightarrow$ | $C_{20}: 4$ |
| Linoleic Acid | | Gamma Linolenic Acid | | Dihomo Gamma-Linolenic Acid | | Arachidonic Acid |

All of these acids are thus particularly indispensable to the normal growth and to the physiological activity of tissue.

The oils rich in essential fatty acids in the form of triglycerides cited above are sunflower oil (57% linoleic acid), corn oil (40% linoleic acid), onagra oil (71% linoleic acid 9% gamma-linolenic acid), borage oil, black currant seed oil.

In man, the conversion of linoleic acid into gamma linolenic acid is a limiting step, which is rendered inoperable by numerous exterior influences. In particular, this step is deficient in the course of aging.

Amongst the essential fatty acids previously noted, the gamma linolenic acid is thus particularly preferred.

The invention has thus in particular as an object compositions characterized in that component B) is a mixture constituted by gamma-linolenic acid in the free form (1), of an oil obtained from a source rich in gamma-linolenic acid (3) and gamma-linolenic acid in the form of alkaline metal or ammonium salts (2), resulting from saponification of (3).

The onagra oil extracted from the seeds of Oenothera Bienis or Oenothera Lamarkiana Bienis plants, the borage oil and the black currant seed oil are three principle vegetable oils rich in gamma-linolenic acids.

Amongst the oils containing gamma-linolenic acid, which can be used in the compositions of the invention, one can likewise cite oil obtained by extraction of siphomycete mushrooms, spirula, maple seed, and hops.

One can utilize, of course, any other oil extract of a natural source of gamma-linolenic acid.

The present invention has in particular as an object compositions characterized in that component B) is a mixture constituted by gamma-linolenic acid in the free form (1), onagra oil (3) and alkaline metal salt of gamma-linolenic acid (2) resulting from the saponification of (3).

The compositions according to the invention can if desired include all substances known as having skin improvement properties such as collagen, elastine, hyaluronic acid, humectants such as urea, pyrrolidone carboxylic acid and its salts, vitamin extracts, perfumes, preservers, coloring agents, spleen or thymus extracts, jojoba oil, karite butter, gamma-oryzanol.

They can also contain small quantities of filters or screens of solar radiation by virtue of the importance of UV radiation on the formation of free radicals of the skin UVA and UVB radiation filters such as for example hydroxy 2—methoxy 4-benzophene, dimethoxy 3, 4-phenyl glyoxylic acid in the form of sodium salt may be used.

The compositions, according to the invention, can be present in any forms utilized in cosmetology cream or gel in jars or tubes, milk, lotion in a glass or plastic flask, and if desired in a measuring flask or a flask provided with a drop counter, or further in vials or in an aerosol spray.

The invention relates thus to cosmetic or dermatological compositions characterized in that they are present in the form of a cream, gel, milk, dermatological cakes, lotion for the skin and for the entire face and for the neck.

In effect, for each form, appropriate vehicles are used. These vehicles must have all of the qualities normally required They must be endowed with a high affinity for the skin, to be perfectly well tolerated, stable, and to present an adequate consistency allowing for an easy and agreeable use.

By way of example of vehicles which can be utilized, one can cite glycerol stearate, propylene glycol, palmitate derivatives, stearates, lanolin, glycerine, cetyl alcohol, polyol, animal oils, mineral oils, waxes, moisturizers, thickeners, stabilizers, and commonly used emulsifiers.

The different cosmetic forms mentioned above are obtained according to conventional methods utilized in this field.

Components A and B of the present invention will be incorporated into the vehicles and the substances having benefits for the skin mentioned above taking into account their affinity for the oil or water phases.

The B components will normally be included from the beginning of the emulsification.

The A components will not be incorporated until the end of the emulsion at a temperature which does not exceed about 35 degrees C.

The invention will now be described with reference to certain non-limiting examples given by way of example only.

EXAMPLE 1

| FLUID GEL | |
|---|---|
| Neutralized Carboxyvinylic Polymer | 0.25–0.65 g |
| Sodium Carboxymethyl Cellulose Salt | 0.02–0.5 g |
| Propylene Glycol | 1.–5. g |
| Polyglycerylmethacrylate Gel | 5.–10. g |
| Perhydrosqualene | 1.–5. g |
| Gamma Oryzanol | 0.05–2. g |
| Alpha Bisabolol | 0.05–0.1 g |
| SKINAVENGER (A Registered Trademark) | 1.–5. g |
| Peptides of high molecular weight | 1.–5. g |
| Hyaluronic Acid | 0.01–0.05 g |
| Preservers | q.s. |
| Perfume | q.s. |
| Coloring Agents | q.s. |
| Purified Water | q.s.p 100 g |

EXAMPLE 2

| OIL/WATER FLUID EMULSION | |
|---|---|
| Stearic Acid | 0.5–2.5 g |
| Propylene Glycol Fatty Acid | 1–5 g |
| Perhydrosqualene | 1–5 g |
| Karite or Cocoa Butter | 1–5 g |
| Polypeptides of Animal Origin | 0.1–1 g |
| Ramified Fatty Esters | 2–12 g |
| UVA/UVB Filter | 0.5–1.5 g |
| Alpha Bisabolol | 0.05–1 g |
| Vegetable Oil | 1–5 g |
| Gamma Oryzanol | 0.05–0.5 g |
| SKINAVENGER (a Registered Trademark) | 1–5 g |
| Hyaluronic acid | 0.01–0.05 g |
| Neutralized Carboxymethylcellulose | 0.1–1 g |
| Propylene Glycol | 3–12 g |
| Urea | 0.5–5 g |
| Preservers | q.s. |
| Perfume | q.s. |
| Purified Water | q.s.p. 100 g |

EXAMPLE 3

| OIL/WATER CREAM | |
|---|---|
| Emulsion Type: | |
| Fatty Ester P.O.E. } Sugars P.O.E. } Phospholipids } | 2–7 g |
| Silicone Oil | 0.5–5 g |
| Vegetable Wax | 0.2–1 g |
| Perhydrosqualene | 1–5 g |
| UVA/UVB Filters | 0.5–1.5 g |
| Cetyl Alcohol | 0.2–1 g |
| Vegetable Oil | 1–5 g |
| Phytosterols | 1–2.5 g |
| Gamma Oryzanol | 0.05–0.5 g |
| Triethanolamine | 0.3–2 g |
| Protein of Animal Origin | 1–5 g |
| SKINAVENGER (a Registered Trademark) | 1–5 g |
| Hyaluronic Acid | 0.01–0.05 g |
| Neutralized Carboxyvinylic Polymer | 0.3–0.8 g |
| Urea | 0.5–5 g |
| Preservers | q.s. |
| Perfume | q.s. |
| Purified Water | q.s.p. 100 g |

EXAMPLE 4

| WATER/OIL CREAM | |
|---|---|
| Glycerol and Sorbitan Isostearate | 10–12 g |
| Perhydrosqualene | 10–15 g |
| 2-ethyl hexyl succinate | 10–15 g |

| WATER/OIL CREAM -continued | |
|---|---|
| Avocado Oil | 3–6 g |
| White Bee Wax | 3–5 g |
| Gamma Oryzanol | 0.05–0.5 g |
| Microcrystalline Wax | 1.–3. g |
| SKINAVENGER (a Registered Trademark) | 1.–5. g |
| Hyaluronic Acid | 0.01–0.03 g |
| Glycerine | 2–5 g |
| Magnesium Sulfite (Mg, SO$_4$, 7H$_2$O) | 0.7 g |
| Preserver | q.s. |
| Perfume | q.s. |
| Purified Water | q.s.p. 100 g |

EXAMPLE 5

| DAY CREAM/FACE CARE | |
|---|---|
| Sorbitan Palmitate | 6.0 g |
| Fatty Acid Glycerides | 13.0 g |
| Vaseline | 4.0 g |
| Oxybenzoin | 1.0 g |
| Onagra Oil | 5.0 g |
| Sorbitol | 3.0 g |
| Neutralized Carboxyvinylic Polymer | 0.5 g |
| Spleen Tissue Extract | 3.0 g |
| FLAVOPHEROL (a Registered Trademark) | 5.0 g |
| Preservers | q.s. |
| Fragrant Composition | q.s. |
| Purified Water | q.s.p. 100 g |

EXAMPLE 6

| HYDRATING DAY CREAM | |
|---|---|
| Cetyl Ether POE | 3.5 g |
| Sorbitan Stearate | 3.5 g |
| Fatty Acid Triglycerides | 5 g |
| Perhydrosqalene | 2 g |
| Hydrogenated Lanolin | 5 g |
| Onagra Oil | 5 g |
| UVA/UVB Solar Filter | 2 g |
| Propylene Glycol | 5 g |
| FLAVOPHEROL (a Registered Trademark) | 3 g |
| Sodium Carboxylate Pyrrolidone | 2 g |
| Neutralized Carboxyvinylic Polymer | 1 g |
| Preservers | q.s. |
| Fragrant Composition | q.s. |
| Purified Water | q.s.p. 100 g |

EXAMPLE 7

| CARE CREAM | |
|---|---|
| Glycerol Stearate and PEG 100 | 6 g |
| Karite Butter | 5 g |
| Onagra Oil | 5 g |
| Cetyl Alcohol | 2 g |
| Fatty Acid Triglycerides | 8 g |
| Vitamin A | 0.5 g |
| Biological Extract | 5 g |
| FLAVOPHEROL (a Registered Trademark) | 5 g |
| Glycerine | 5 g |
| Neutralized Carboxyvinylic Polymer | 1 g |
| Preservers | q.s. |
| Fragrant Composition | q.s. |
| Purified Water | q.s.p. 100 g |

EXAMPLE 8

| FACE GEL | |
|---|---|
| AGE in the form of liposomes | 0.5 g |
| FLAVORPHEROL (a Registered Trademark) | 3 g |
| Sodium Carboxylate Pyrrolidone | 2 g |
| Preserver | q.s. |
| Fragrant Composition | q.s. |
| Neutralized Carboxyvinylic Polymer | 1.5 g |
| Propylene Glycol | 5 g |
| Purified Water | q.s.p. 100 g |

EXAMPLE 9

| SUN PROTECTION CREAM | |
|---|---|
| Vaseline Oil | 5 g |
| Silicone Oil | 1 g |
| Fatty Acid Ester | 5 g |
| Lanolin Derivative | 8 g |
| Glycerol Stearate and PEG 100 | 6 g |
| UVA and UVB Sun Filter | 5 g |
| Onagra Oil | 3 g |
| Sorbitol | 5 g |
| FlAVOPHEROL (a Registered Trademark) | 3 g |
| Inorganic Mineral Pigments | 5 g |
| Neutralized Carboxyvinylic Polymer | 1 g |
| Preservers | q.s. |
| Fragrant Composition | q.s. |
| Purified Water | q.s.p. 100 g |

Although the invention has been described with reference to particular means, compositions, and embodiments, it is to be understood that the invention is not limited to particulars disclosed and extends to all equivalents within the scope of the claims.

We claim:

1. A composition for skin care comprising:
   (a) a first component comprising *Silybum Marianum* fruit extract; and
   (b) another component comprising at least one essential polyunsaturated fatty acid containing 18-22 carbon atoms provided by a mixture of:
     (i) a free form of said fatty acid;
     (ii) a salt of said fatty acid selected from the group consisting of alkaline metal salts of said fatty acid and ammonium salts of said fatty acid; and
     (iii) triglycerides comprising said fatty acids.

2. The composition of claim 1, wherein said salt of said fatty acid is a saponification product of said triglycerides.

3. The composition of claim 1, wherein said essential polyunsaturated fatty acid is formed from vegetable oils selected from the group consisting of wheat germ oils, olive oils, corn oils, sunflower oils, sweet almond oils, onagra of borage, and black currant seeds.

4. The composition of claim 1, wherein said mixture comprises:
   (i) a free form of gamma-linoleic acid;
   (ii) a salt of gamma-linoleic acid selected from the group consisting of alkaline metal salts of gamma-linoleic acid ammonium salts of gamma-linoleic acid; and
   (iii) a triglyceride oil obtained from a source rich in gamma-linoleic acid.

5. The composition of claim 4, wherein said oil obtained from a source rich in gamma-linoleic acid is selected from the group consisting of onagra oil, borage oil, black currant seed oil, and oil obtained by extraction of siphomycete mushrooms, spirula, maple seed, and hops.

6. The composition of claim 1, wherein said first component further comprises a member selected from the group consisting of essential terpene oils, flavonoids, and alpha-tocopherols, and mixtures of two or more of terpene oils, flavonoids, and alpha-tocopherols.

7. The composition of claim 6, wherein said member is an essential terpene oil.

8. The composition of claim 6, wherein said member is a flavinoid.

9. The composition of claim 6, wherein said member is an alpha-tocopherol.

10. A composition for skin care comprising:
    (a) a first component comprising:
      (i) about 10-30% by weight of *Silybum Marianum* extract;
      (ii) about 5-15% by weight of essential terpene oils;
      (iii) about 5-15% by weight of flavonoids; and
      (iv) about 5-20% by weight of alpha-tocopherol; and
    (b) another component comprising:
      (i) about 25-40% by weight of essential fatty acid triglycerides;
      (ii) about 10-25% of a free form of essential fatty acids; and
      (iii) a salt of essential fatty acid.

11. The composition of claim 10, wherein one of said essential fatty acid triglycerides is borage oil.

12. The composition of claim 11, wherein said salts of essential fatty acids are selected form the group consisting of alkaline metal salts of essential fatty acids and ammonium salts of essentially fatty acids.

13. The composition of claim 12, wherein said salts of essential fatty acids are a saponification products of onagra oil.

14. The composition of claim 12, wherein said essential fatty acids comprise onagra oil, said free form of essentially fatty acid is a free form of gamma-linoleic acid, and said salt of essential fatty acid is an alkaline metal salt of gamma-linolenic acid.

15. The composition of claim 14, wherein said alkaline metal salt is a saponification product of onagra oil.

16. A composition for skin care comprising a mixture of:
    (a) about 1-10% by weight onagra oil; and
    (b) about 1-10% by weight of a mixture of:
      (i) about 5% of delipidated fruit of Silybum Marianum; and
      (ii) about 0.05-2% by weight of alpha-tocopherol in polyethylene glycol.

17. A composition for skin care comprising a mixture of:
    (a) about 5% by weight onagra oil; and
    (b) about 5% by of a mixture of:
      (i) about 5% of delipidated fruit of *Silybum Marianum*;
      (ii) about 1% by weight of alpha-tocopherol in polyethylene glycol;
      (iii) about 1-10% by weight of UVA-UVB sun filters; and
      (iv) about 1-10% by weight of spleen extract.

18. A gel composition comprising:
    (a) a component comprising *Silybum Marianum* fruit extract; and
    (b) another component comprising at least one essential polyunsaturated fatty acid containing 18-22 carbon atoms provided by a mixture of:

(i) a free form of said fatty acid;
(ii) a salt of said fatty acid selected from the group consisting of alkaline metal salts of said fatty acids and ammonium salts of said fatty acids; and
(iii) triglycerides comprising said fatty acids.

19. A creme composition comprising:
(a) a component comprising *Silybum Marianum* fruit extract; and
(b) another component comprising at least one essential polyunsaturated fatty acid containing 18-22 carbon atoms provided by a mixture of:
(i) a free form of said fatty acid;
(ii) a salt of said fatty acid selected from the group consisting of alkaline metal salts of said fatty acids and ammonium salts of said fatty acids; and
(iii) triglycerides comprising said fatty acids.

20. A milk composition comprising:
(a) a component comprising *Silybum Marianum* fruit extract; and
(b) another component comprising at least one essential polyunsaturated fatty acid containing 18-22 carbon atoms provided by a mixture of:
(i) a free from of said fatty acid;
(ii) a salt of said fatty acid selected from the group consisting of alkaline metal salts of said fatty acids and ammonium salts of said fatty acids; and
(iii) triglycerides comprising said fatty acids.

21. A skin lotion composition comprising:
(a) a component comprising *Silybum Marianum* fruit extract; and
(b) another component comprising at least one essential polyunsaturated fatty acid containing 18-22 carbon atoms provided by a mixture of:
(i) a free form of said fatty acid;
(ii) a salt of said fatty acid selected from the group consisting of alkaline metal salts of said fatty acids and ammonium salts of said fatty acids; and
(iii) triglycerides comprising said fatty acids.

* * * * *